US009724530B2

(12) United States Patent
Edwards et al.

(10) Patent No.: US 9,724,530 B2
(45) Date of Patent: Aug. 8, 2017

(54) USER INTERFACE METHOD AND APPARATUS FOR A MEDICAL DEVICE

(71) Applicant: Physio-Control, Inc., Redmond, WA (US)

(72) Inventors: D. Craig Edwards, Fall City, WA (US); Kelly J. Locke, Woodinville, WA (US); Mark B. Gausman, Bellevue, WA (US); Alex Otman, Bothell, WA (US); Richard C. Nova, Kirkland, WA (US); Shawn R. Bertagnole, Lake Stevens, WA (US)

(73) Assignee: Physio-Control, Inc., Redmond, WA (US)

( * ) Notice: Subject to any disclaimer, the term of this patent is extended or adjusted under 35 U.S.C. 154(b) by 704 days.

(21) Appl. No.: 14/015,398

(22) Filed: Aug. 30, 2013

(65) Prior Publication Data

US 2013/0345769 A1 Dec. 26, 2013

Related U.S. Application Data

(63) Continuation of application No. 10/147,241, filed on May 15, 2002, now Pat. No. 8,527,044.

(51) Int. Cl.
*A61N 1/39* (2006.01)

(52) U.S. Cl.
CPC .................... *A61N 1/3993* (2013.01)

(58) Field of Classification Search
CPC ...... A61N 1/39; A61N 1/3968; A61N 1/3993; A61H 2201/5007; A61H 2201/5043; A61H 2201/5048
USPC ............................... 607/4, 5, 9, 10
See application file for complete search history.

(56) References Cited

U.S. PATENT DOCUMENTS

2003/0208237 A1* 11/2003 Locke et al. ................ 607/5

* cited by examiner

*Primary Examiner* — Rex R Holmes
(74) *Attorney, Agent, or Firm* — Lane Powell PC

(57) ABSTRACT

A user interface method and apparatus is described for use with a defibrillator (100) such as an automated external defibrillator (AED). The user interface comprises a plurality of layered user interface components which become available to the operator of the defibrillator (100) as they become necessary or appropriate during the operation of the defibrillator (100) and treatment of the patient. In one embodiment, the layered user interface components comprise an on/off actuator (108), a lid (104), an electrode package (120) containing defibrillation electrodes (142, 144), and a shock key (170), as well as accompanying visual and aural instructions for operating the defibrillator (100) and for treating the patient.

15 Claims, 12 Drawing Sheets

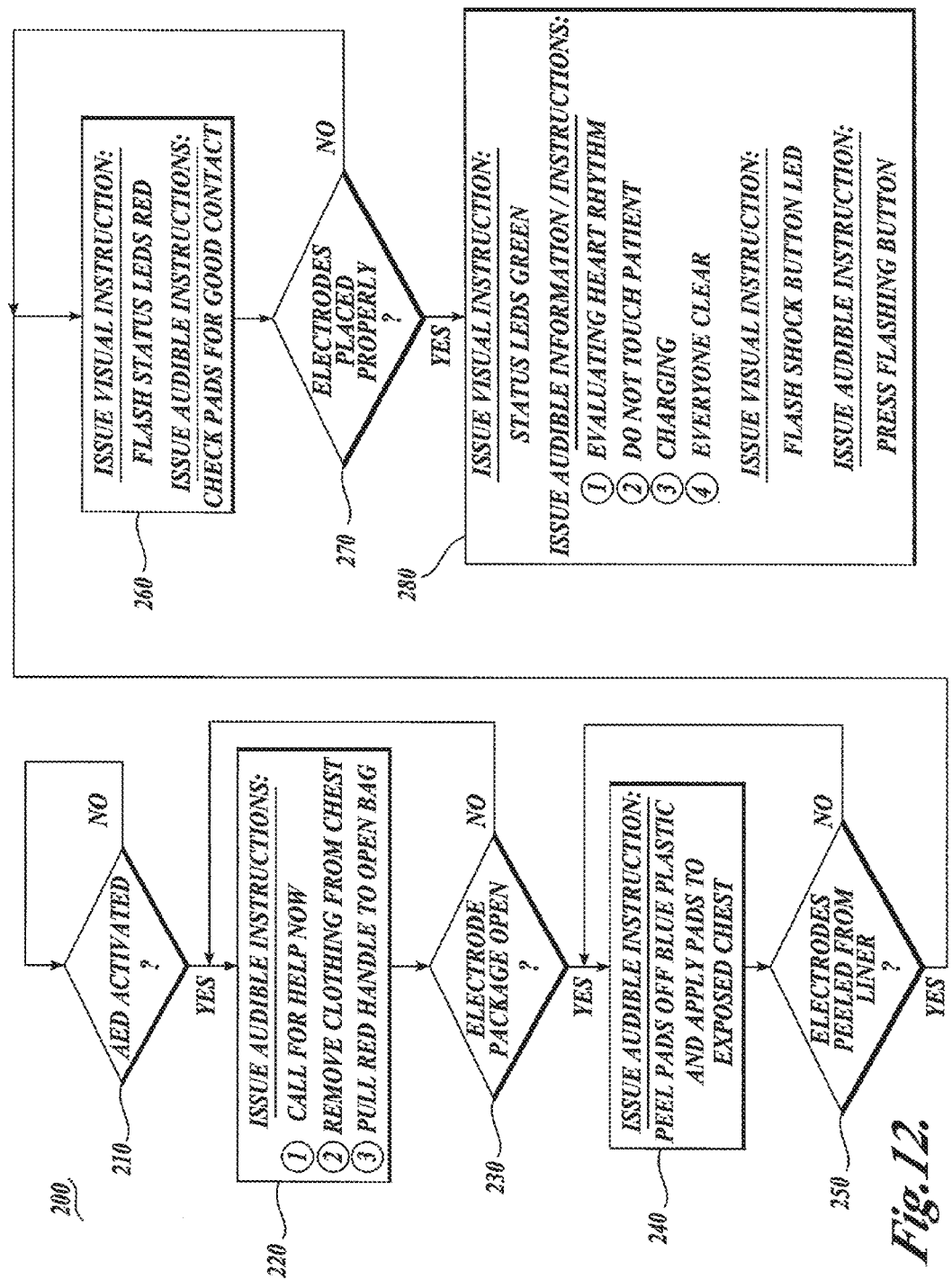

USER INTERFACE METHOD AND APPARATUS FOR A MEDICAL DEVICE

CROSS-REFERENCE TO RELATED APPLICATION

This application is a continuation of U.S. patent application Ser. No. 10/147,241, filed May 15, 2002, which issued on Sep. 3, 2013 as U.S. Pat. No. 8,527,044, the content of which is hereby fully incorporated by reference herein.

FIELD OF THE INVENTION

The present invention relates generally to a user interface method and apparatus for a medical device, and more particularly to a user interface method and apparatus for a defibrillator.

BACKGROUND OF THE INVENTION

Sudden cardiac death is the leading cause of death in the United States. Most sudden cardiac deaths are caused by ventricular fibrillation, in which the heart's muscle fibers contract without coordination, thereby interrupting normal blood flow into the body. The best known effective treatment for ventricular fibrillation is electrical defibrillation, in which an electrical pulse is applied to the patient's heart. The electrical pulse must be delivered within a short time after onset of ventricular fibrillation in order for the patient to have any reasonable chance of survival.

The current trend in the medical industry is to make life-saving portable medical devices, such as automated external defibrillators (AEDs), more widely accessible so that patients in need can be treated as quickly as possible. As the availability of portable medical devices continues to increase, more places will have these devices for use in emergency situations, such as in homes, police cars, worksites, and public gathering places. This increase also comes with the heightened likelihood that these portable medical devices will be used by people without medical training or people who are minimally trained in the handling of the medical devices. At the same time, the benefit of having life-saving medical devices immediately available in many places is not fully realized unless the medical devices can be promptly activated and used quickly in case of emergency. Therefore, a portable medical device, such as an AED, must be configured such that even a lay person can intuitively and quickly activate and use the medical device.

A medical device may automatically instruct an operator how to properly operate the medical device via various user interface components. For example, an AED may include a voice command system, a screen command system, and/or various graphics visible to the operator. Additional user interface components may also be available. For example, an AED typically includes a pair of defibrillation electrodes to be applied by an operator on the patient's body. Ideally, various user interface components should be immediately available to the operator of a medical device so that the operator can access or follow instructions offered by the user interface components to operate the medical device to save the patient's life. At the same time, some of the user interface components should be made available to the operator at the appropriate points during treatment of the patient in order to ensure that an instructional command, for example a voice prompt, of the medical device can timely guide the operator how to properly operate the device and treat the patient. This feature can be particularly helpful when the medical device is likely to be used by a lay person who is not very familiar with the medical device and thus needs to rely on commands issued by the medical device to properly handle the medical device.

SUMMARY OF THE INVENTION

In accordance with the present invention, a method and apparatus is disclosed for providing a layered user interface for an operator of a portable medical device, meaning that instructions concerning a series of operations to be performed by the operator for the treatment of a patient using the medical device, along with user interface tools to perform those operations, are provided to the operator as each of the operations becomes necessary or appropriate for treatment.

In one aspect of the invention, the medical device is a defibrillator, and a layered user interface is provided that includes an activation layer, an electrode application layer, and a defibrillation pulse delivery layer. The activation layer guides the operator to activate the defibrillator, and may include an on/off button. The electrode application layer is made available to the operator subsequent to the activation layer, and guides the operator to apply electrodes to the patient. The electrode application layer may include an electrode package containing the electrodes, and instructions concerning opening the package and applying the electrodes to the patient. The defibrillation pulse delivery layer is made available to the operator subsequent to the electrode application layer, and guides the operator through delivery of a defibrillation pulse to the patient. The defibrillation pulse delivery layer may include a shock key that the operator presses to initiate delivery of the defibrillation pulse, and instructions concerning actuating the shock key.

In another aspect of the invention, a method for providing a user interface to an operator of an external defibrillator includes first drawing the attention of the operator to an actuator for activating the defibrillator. Upon the defibrillator being activated, an electrode package containing defibrillation electrodes is revealed to the operator, along with instructions for deploying the electrode package. Upon the electrode package being deployed, a shock key is revealed to the operator, along with instructions for actuating the shock key to initiate delivery of a defibrillation pulse. The various provided instructions may include visual, audible, written, or diagrammatic instructions.

In a further aspect of the invention, a method for providing a user interface to an operator of an external defibrillator includes first instructing the operator concerning activating the defibrillator. Once the defibrillator is activated, the operator is provided with an electrode package having an opener that is actuatable by the operator. The operator is instructed concerning opening the electrode package, and upon the operator opening the electrode package, the operator is instructed concerning removal of electrodes from the electrode package. Upon the operator removing the electrodes from the electrode package, the operator is instructed concerning the positioning of the electrodes on the patient. Upon the operator positioning the electrodes on the patient, the operator is instructed concerning subsequent care giving operations. In various aspects of the invention, the series of instructions provided to the operator includes written information, audible information, or color and diagrams relating to the successive operations to be performed by the operator of the defibrillator. The operator may also be provided with status information concerning the positioning of the electrodes on the patient, such as by providing the operator with visual status signals or with audible instructions prompting the operator to check the positioning of the electrodes.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 12 is a flow diagram depicting a prompting routine executed by the defibrillator to deliver visual and aural instructions to the operator.

DETAILED DESCRIPTION OF THE PRESENT INVENTION

In accordance with the present invention, a user interface is provided for a portable medical device comprising a plurality of layered user interface components. The user interface components are layered so as to become available to the operator of the device as they become necessary or appropriate during the operation of the device and treatment of the patient. Stated another way, the user interface components are layered to successively provide the operator with instructions and implements for operating the device and treating the patient. In the present description, the term "user interface component" is used to encompass any message and or/instruction sent to or received from the operator of the medical device, any device component or accessory used to send or receive such messages/instructions, and any implement that is physically used by the operator for operation of the device or treatment of the patient.

Figure 1:
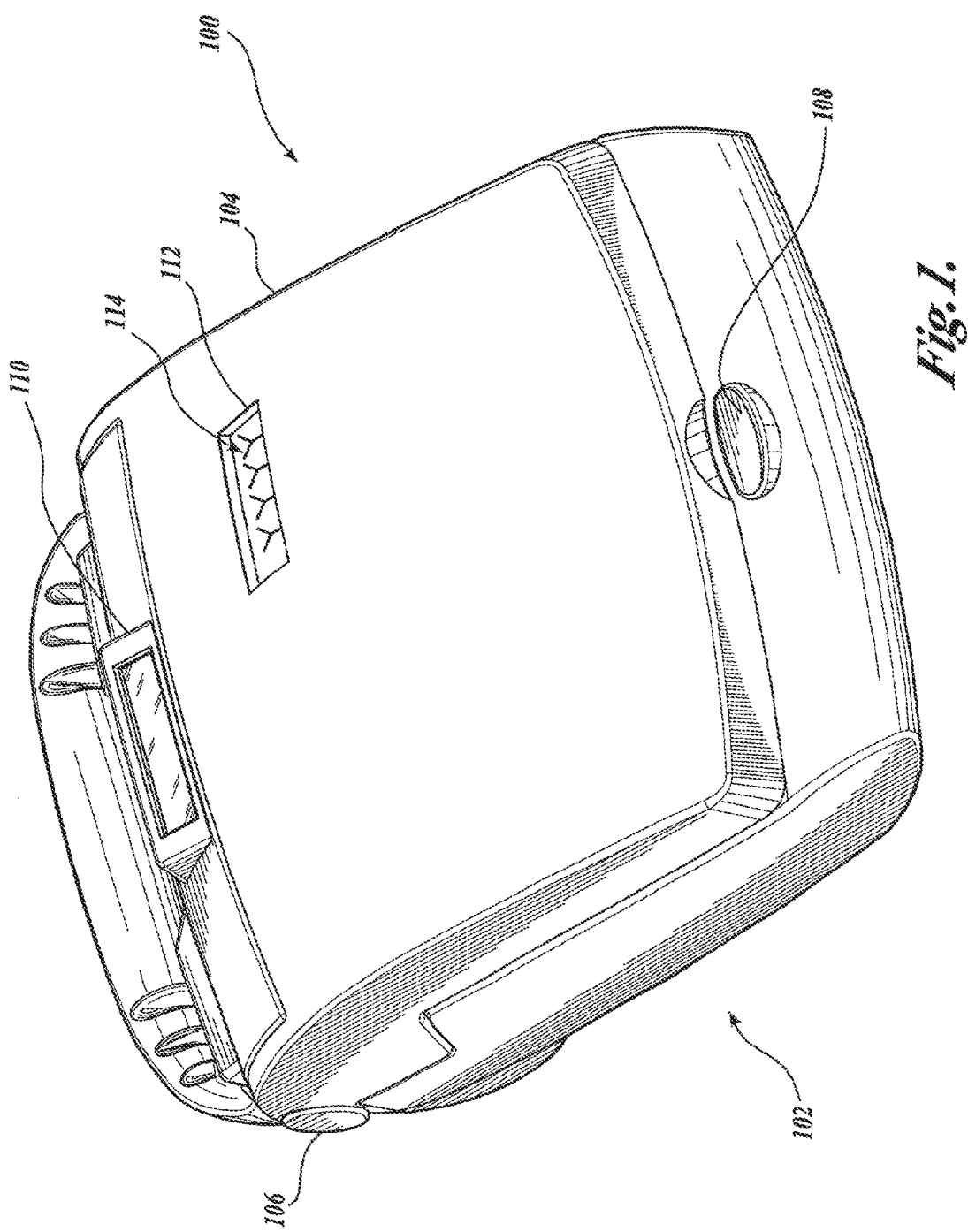
FIG. 1 is a perspective view of a medical device comprising a defibrillator which incorporates a layered user interface in accordance with the present invention.

FIG. 1 illustrates a medical device embodied as a portable automated external defibrillator (AED) 100, suitable for incorporating the layered user interface of the present invention. Although a defibrillator is used to describe this embodiment, in light of this disclosure, those skilled in the art will be able to implement the present invention with other types of medical equipment without undue experimentation. Further, in the following description certain specific details are set forth in order to provide a thorough understanding of various embodiments of the present invention. One skilled in the art will understand, however, that the present invention may be practiced without these details. In other instances, well-known functions, features, and operations of AEDs have not been shown or described in detail in order to avoid unnecessarily obscuring the description of the various embodiments of the present invention.

Returning to FIG. 1, an AED 100 incorporating a layered user interface formed in accordance with the present invention is depicted. As depicted in the illustrated embodiment, the user interface components of the layered user interface may comprise an on/off actuator 108, a lid 104, an electrode package 120 (see FIG. 3) and a shock key 170 (see FIG. 6), as well as accompanying visual and/or audible instructions for operating the AED and for treating the patient. As will be appreciated from the following description, beginning with the on/off actuator 108, each successive user interface component will become available to the operator as it becomes necessary for use by or instruction to the operator.

Figure 2:
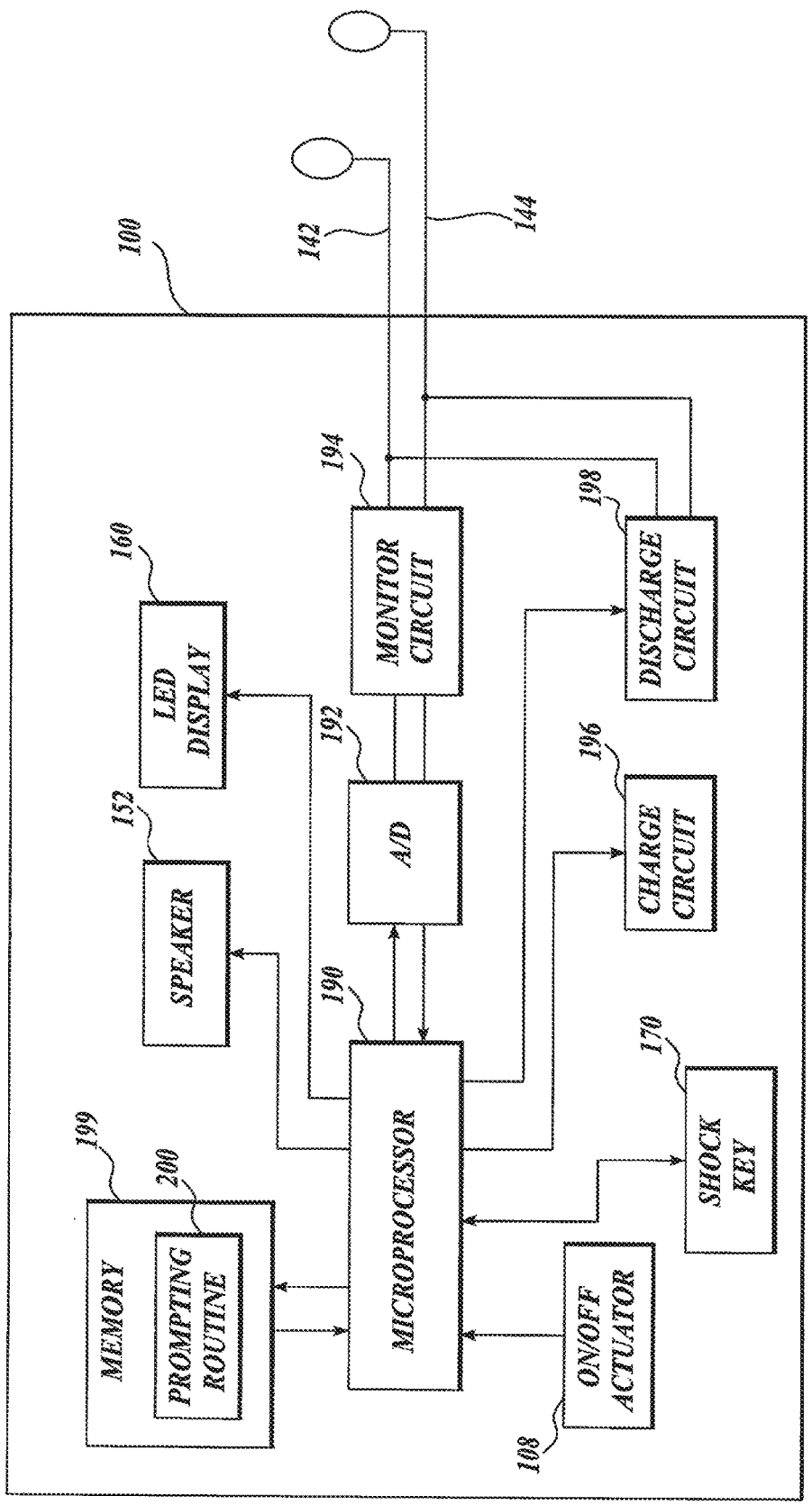
FIG. 2 is a schematic block diagram of several of the key components of the defibrillator shown in FIG. 1.

As shown in FIG. 1, the AED 100 includes a housing 102 containing the electronics necessary for the operation of the AED 100, as will be described in more detail below. As shown in more detail in FIG. 2, the AED 100 includes a microprocessor 190 which controls the operation of the AED 100. The microprocessor 190 is connected to an LED display 160, a speaker 152, an on/off actuator 108, and a shock key 170. The microprocessor 190 is also connected to a memory 199 which stores a prompting routine 200 (see FIG. 12) formed in accordance with the present invention to generate visual instructions upon the display 160 and any accompanying aural instructions transmitted via the speaker 152. In yet other embodiments of the present invention, the memory stores a voice recognition software module which allows the rescuer to operate the AED 100 and respond to visual and/or aural instructions via voice command rather than using the start and shock buttons. Such a module in combination with a microphone would then provide the rescuer with hands-free operation of the AED 100.

During defibrillation operation, the microprocessor 190 analyzes an electrocardiogram (ECG) of a patient using an automatic heart rhythm detection algorithm also stored in the memory 199 to identify whether the patient is experiencing a shockable heart rhythm, such as ventricular fibrillation. The detection algorithm executed by the microprocessor 190 in the actual embodiment of the present invention described herein is similar to that used in the LIFEPAK® 500 defibrillator provided by Medtronic Physio-Control Corp. of Redmond, Wash. Other known heart rhythm detection algorithms may also be used without departing from the scope of the present invention, such as those algorithms designed to comply with standards promulgated by the Association for the Advancement of Medical Instruments (AAMI). The ECG signals analyzed by the detection algorithm are collected by defibrillation electrodes 142, 144 and passed through a monitor circuit 194 to an analog-to-digital converter 192. The analog-to-digital converter 192 then passes the digitized signals to the microprocessor 190. If the microprocessor 190 detects a shockable rhythm, the microprocessor causes a charge circuit 196 to generate a current causing a storage capacitor (not shown) to charge in preparation for delivery of a defibrillation pulse. When the capacitor is fully charged, and delivery of the defibrillation pulse initiated, a discharge circuit 198 coupled to the microprocessor 190 and charge circuit 196 discharges the defibrillation pulse to the defibrillation electrodes 142, 144 for application of the defibrillation pulse to the patient.

Figure 3:
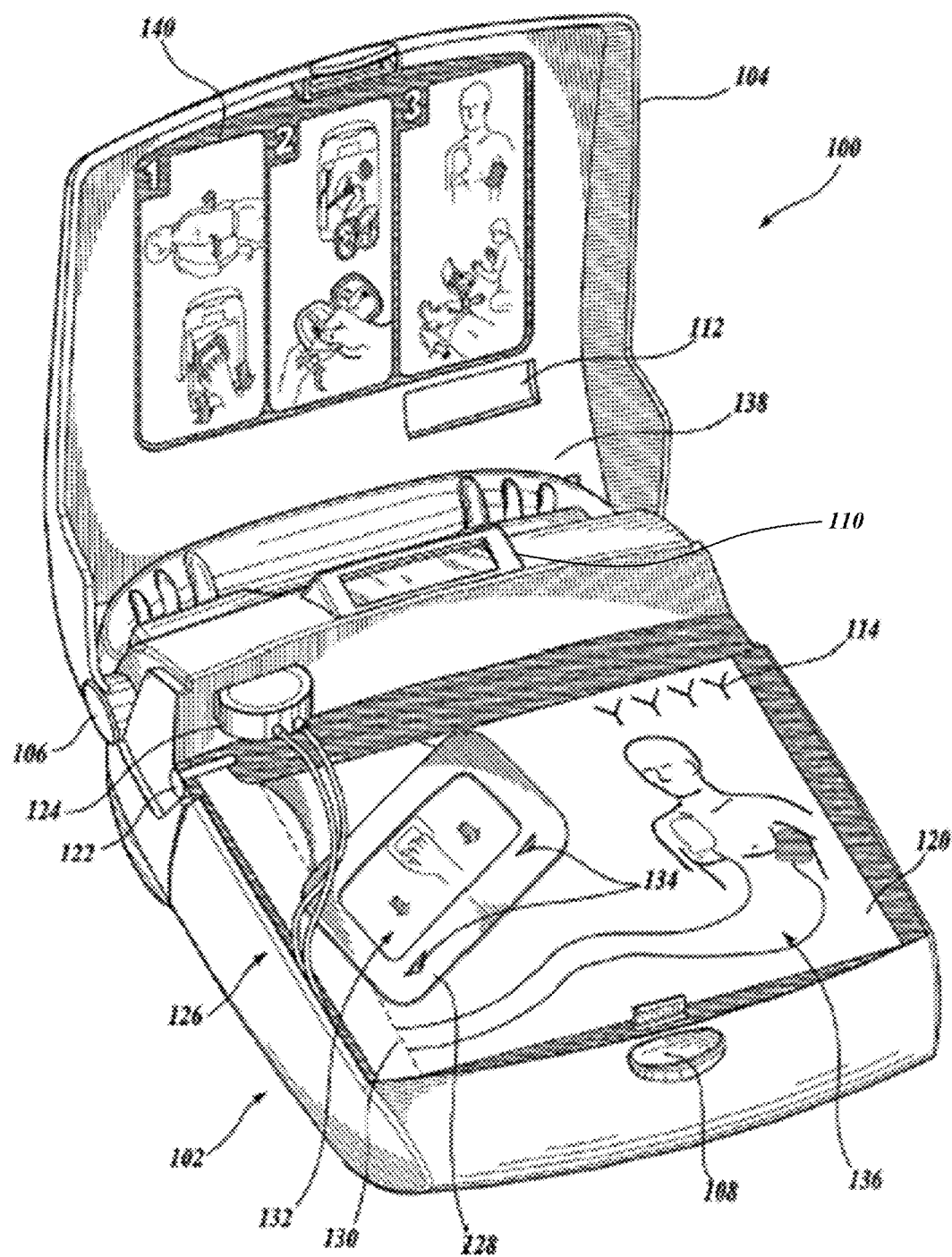
FIG. 3 depicts the defibrillator of FIG. 1 wherein a lid of the defibrillator is opened, revealing an electrode package having a handle previously hidden beneath the lid.

Returning to FIG. 1, the AED housing 102 includes an on/off actuator 108 which is sized and colored so as to attract the operator's attention as the first action required to use the AED 100. For example, in one embodiment, the on/off actuator 108 is large in size (relative to its required mechanical function) and colored bright yellow to visually contrast with the substantially gray/black colored lid 104 of the AED 100. Though the on/off actuator 108 is illustrated to be in the form a button, the actuator may take various other shapes and forms, for example, a membrane, plate, bar, etc., as long as it is adapted to receive an operator's instruction to activate the AED 100. In one embodiment, the on/off actuator 108 is configured so that depressing it sequentially activates the AED 100 and opens the next user interface component, i.e., a lid 104. The lid 104 is pivotally coupled to the housing 102 at two pivot points 106 in a conventional manner, so that the lid 104 can be opened as shown in FIG. 3. Alternatively, movement of the lid 104 to an open position can be the event activating the AED 100. Indeed, one skilled in the art will appreciate that the presence of the on/off actuator 108 is optional, and the AED 100 could instead be activated by the operator opening the lid 104, or by another operator-initiated action. Such single-action methods and systems for activating medical devices are described in more detail in U.S. application Ser. No. 10/139,942, filed May 6, 2002, entitled "Single-Action Method of Activating and Exposing User Interface of Medical Device," and specifically incorporated herein by reference. Activation of the medical device by any of these or other methods or systems may be referred to in the context of the present invention as an "activation layer" of the layered user interface.

FIG. 3 illustrates the AED 100 of FIG. 1 when the lid 104 is opened, bringing the operator to the next layer of user interface component that is appropriate for use at this point in the operation of the device and the treatment of the patient, i.e., opening the lid 104 brings the operator to an electrode package 120 positioned within the housing 102 beneath the lid 104. In one embodiment, the electrode package 120 is a bag attached to the housing 102 by an anchor pin 122. Contained within the electrode package 120 are a pair of defibrillation electrodes (not shown in FIG. 3) that are electrically coupled with monitoring and defibrillation circuitry inside the housing 102 by an electrode connector 124 and electrode wires 126.

As will be appreciated by those skilled in the defibrillator arts, once an AED is activated, the next step in its operation is typically to apply a pair of defibrillation electrodes to the patient's chest that are used to monitor the patient's heart rhythm and deliver a defibrillation pulse is necessary. Accordingly, in one embodiment of the present invention, the electrode package 120 is positioned beneath the lid 104 and sized so as to attract the operator's immediate attention as the next appropriate action to take in the operation of the device and treatment of the patient. To further intuitively guide the operator in the correct operation and application of the electrodes, the electrode package 120 includes a package opening member, such as handle 128, which the operator pulls to open the electrode package along a tear line 130 and release the defibrillation electrodes packaged therein. To further bring attention to the handle, the handle is configured and colored to be conspicuous to the operator. For example, in one embodiment the handle 128 is large in size (relative to its required mechanical function) and colored bright red to visually contrast with the substantially white colored electrode package 120. Also, the handle has a skew orientation—i.e., not aligned parallel with the sides of the substantially rectangular electrode package 120—which further visually attracts the operator's attention. Still further, the handle 128 itself may include diagrammatic arrows 134 indicating the direction the operator should pull the handle and the upper surface of the electrode package 120 may include a graphical diagram 132 depicting how the operator should grasp and pull the handle 128 in order to open the electrode package 120 (as well as a patient diagram 136 that depicts the appropriate placement of the defibrillation electrodes on the chest of a patient).

In addition to the size, configuration, color and placement of the electrode package 120 and the handle 128, the AED 100 may issue audible instructions to the operator upon opening of the lid 104 to pull the handle 128 to open the electrode package 120, as well as audible instructions to first call for help and remove clothing from the patient's chest. It will be appreciated by those skilled in the art that although highly desirable, such audible instructions may be omitted without departing from the spirit and scope of the present invention.

Figure 4:
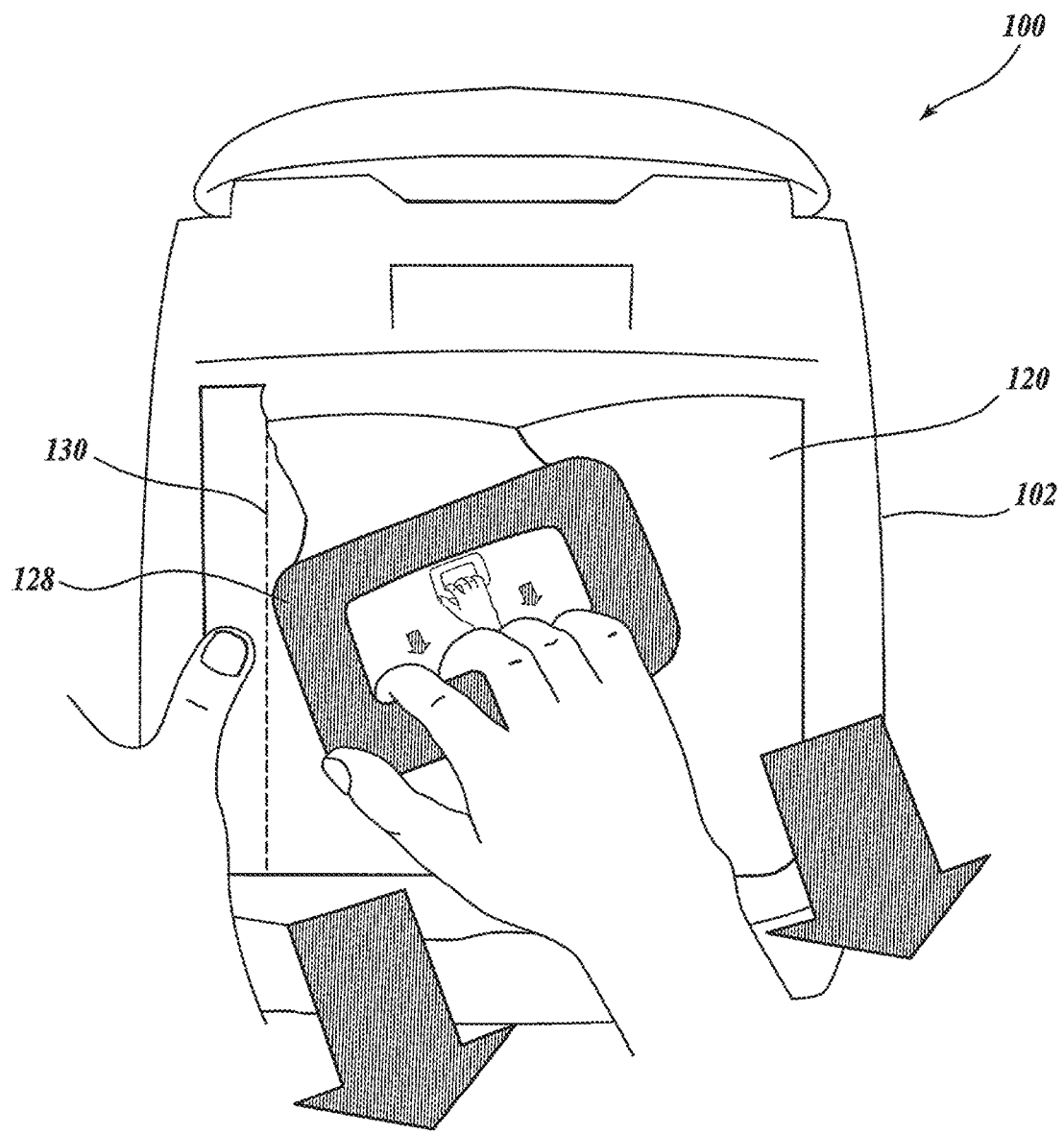
FIG. 4 depicts an operator of the defibrillator opening the electrode package by grasping and pulling the handle.
Figure 5:
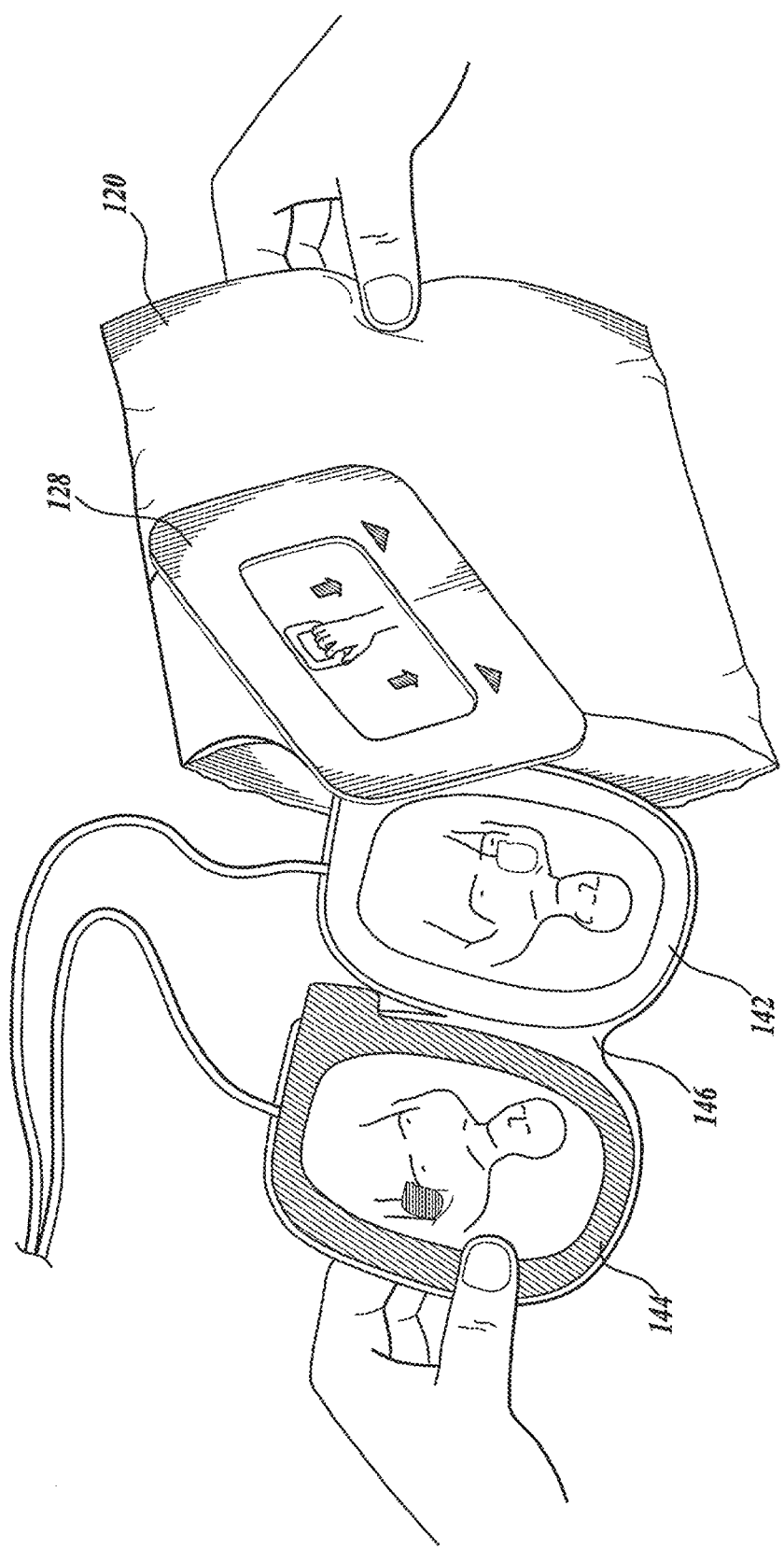
FIG. 5 depicts the operator removing defibrillation electrodes from the opened electrode package.
Figure 6:
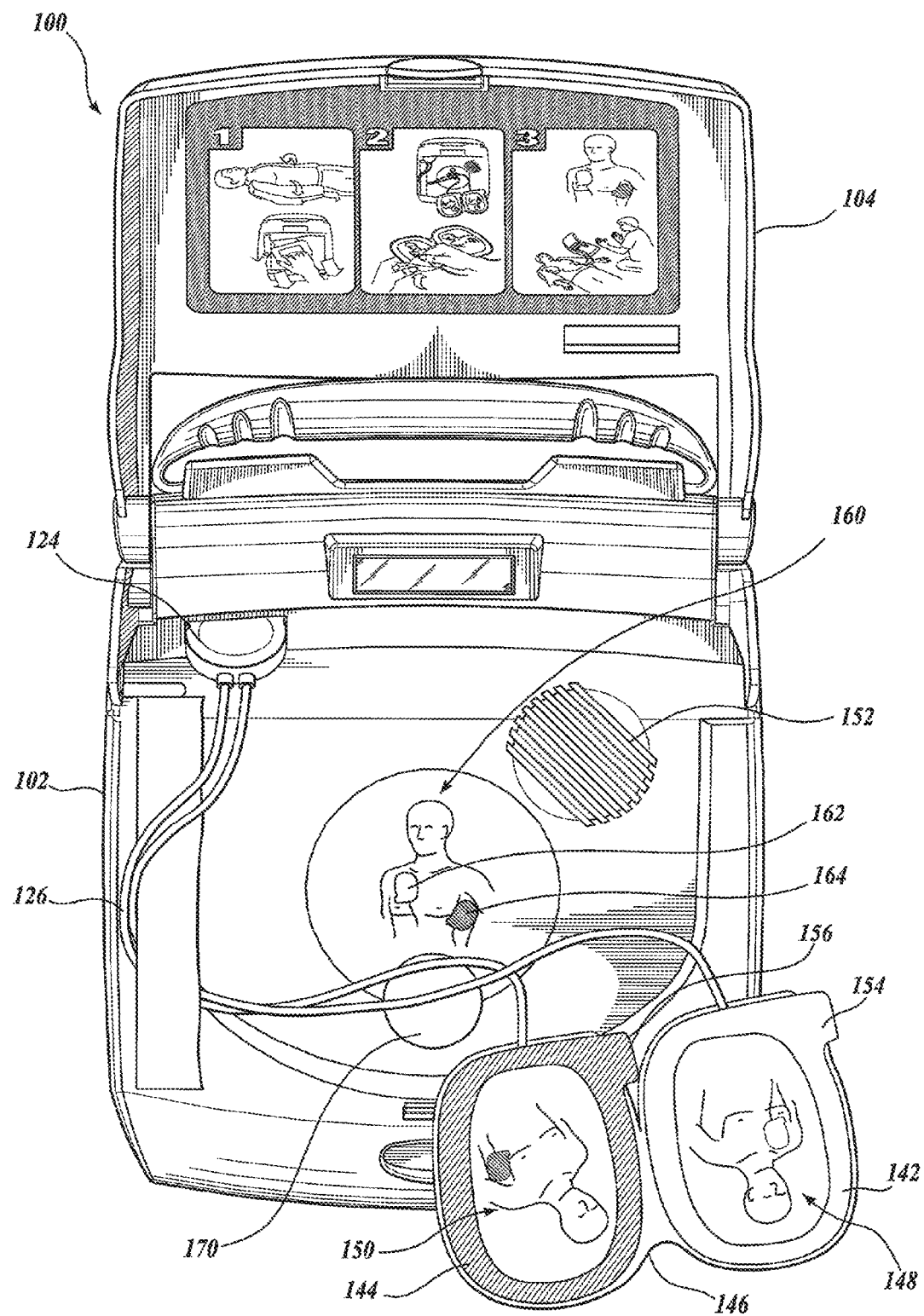
FIG. 6 depicts the defibrillator after the defibrillation electrodes have been removed from the electrode package, now discarded.
Figure 7:
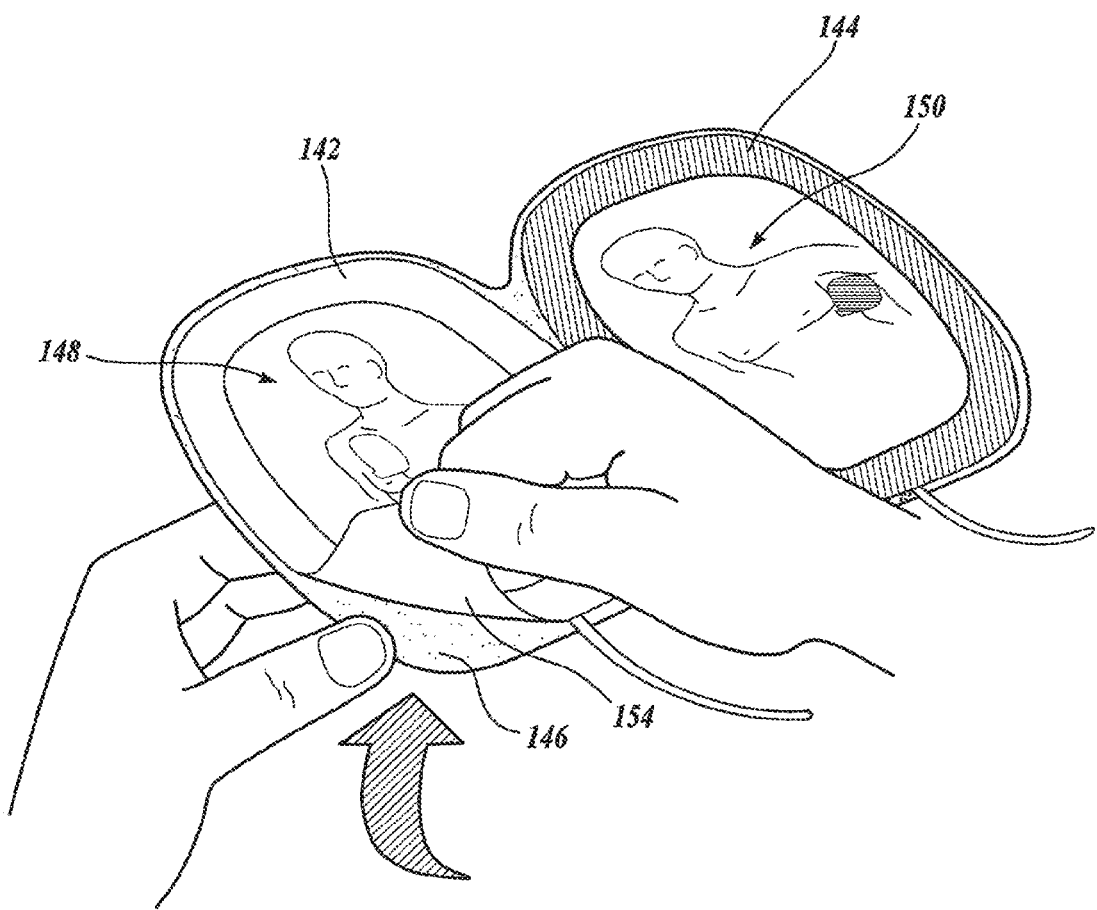
FIG. 7 depicts the operator removing an electrode pad from a liner sheet on which the defibrillation electrodes are removably adhered.

FIG. 4 depicts the operator pulling on the handle 128 in order to open the electrode package 120 along the tear line 130. FIG. 5 then shows the operator removing the defibrillation electrodes 142, 144 (also commonly referred to as electrode pads) from the electrode package 120. Referring now to FIG. 6, the AED 100 is shown after the defibrillation electrodes 142, 144 have been removed from the opened electrode package 120 (which the operator has discarded or otherwise set aside, and is not shown in FIG. 6). The operator is now presented with the next layer of user interface component, namely, the defibrillation electrodes 142, 144 themselves. In the embodiment shown in FIG. 7, the defibrillation electrodes 142, 144 are positioned on a single pad liner 146 of contrasting color to that of the electrodes. (Those skilled in the art will appreciate that the defibrillation electrodes could instead be positioned on separate liners or in other suitable configurations.) For example, the defibrillation electrodes 142 and 144 may have respectively colored boundaries of yellow and red, with the liner 146 being blue-colored plastic. It has been found that lay persons unfamiliar with the use of AEDs or medical devices often do not realize that defibrillation electrodes include a layer of gel covered by a liner that must be removed in order to reveal the gel and affix the electrode to the patient. The different colors of the electrodes and the liner, along with the disposition of the defibrillation electrodes 142, 144 together on a single liner 146, intuitively emphasize to the operator that the defibrillation electrodes must be separated from one another and from the liner in order to be applied.

To further guide the operator in releasing the liner from the electrodes, each of the defibrillation electrodes 142 and 144 has a respective one of tabs 154 and 156 (see also FIG. 6), which the operator grasps and pulls in order to remove the defibrillation electrodes from the liner 146. The tabs 154, 156 may include diagrammatic arrows that visually indicate to the operator to pull the tabs. In addition, the tabs 154, 156 are large and protrude beyond the boundary of the liner 146, so as to be visually obvious to the operator.

To further guide the operator in the placement of the electrodes once separated from one another and removed from the liner 146, the defibrillation electrodes 142 and 144 include pad placement diagrams 148 and 150, respectively, which illustrate for the operator the proper location for each electrode on the patient. In one embodiment, each pad placement diagram depicts the proper location of only its corresponding pad, it does not depict both pads. Proper placement of each electrode is further intuitively encouraged by placing the defibrillator electrode 142 intended for placement on the left side of the patient (from the operator's perspective) on the left side of the liner 146, and placing the defibrillator electrode 144 intended for placement of the right side of the patient on the right side of the liner 146. Proper placement is encouraged further by coloring the boundaries of the defibrillation electrodes 142 and 144 differently (e.g., yellow and red as mentioned above) and by using corresponding colors in the pad placement diagrams 148 and 150.

In addition to the size, configuration, color and placement of the defibrillation electrodes 142 and 144 and the liner 146, the AED 100 may issue additional audible instructions to the operator via an audio speaker 152 to remove each of the defibrillation electrodes 142, 144 from the liner 146 and to then apply the defibrillation electrodes to the exposed chest of the patient. It will be appreciated by those skilled in the art that although highly desirable, such audible instructions may be omitted without departing from the spirit and scope of the present invention.

Figure 8:
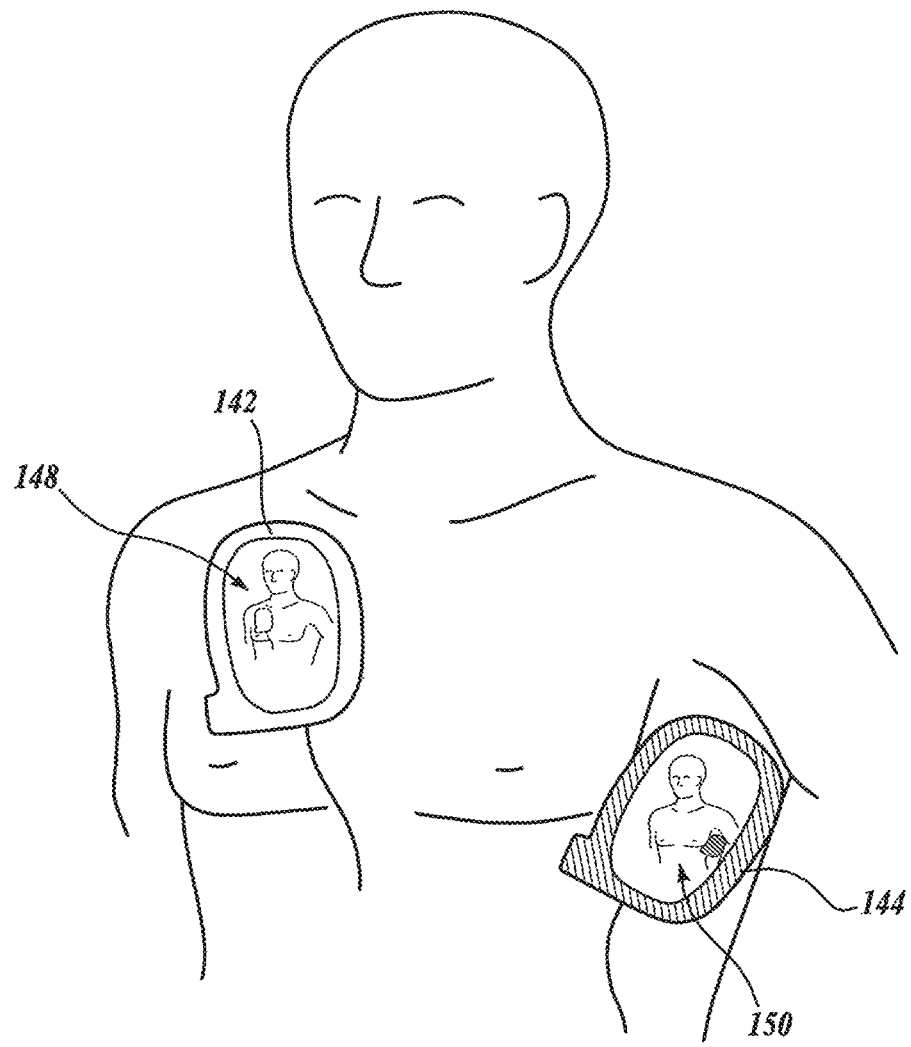
FIG. 8 depicts proper placement of the defibrillation electrodes on the exposed chest of a patient.

FIG. 8 depicts the proper placement of the defibrillation electrodes 142, 144 on the exposed chest of the patient, consistent with the colors of the defibrillation electrodes, the positioning of the defibrillation electrodes on the liner, the pad placement diagrams 148, 150 on the defibrillation electrodes, and the audible instructions. The deployment of the electrode package 120 and the defibrillation electrodes 142, 144 as, for example, described above, may be referred to in the context of the present invention as an "electrode application layer" of the layered user interface.

Returning to FIG. 6, once the electrode package 120 is removed from the AED 100, the next layer of user interface component made available to the operator is the shock key 170 and an electrode status display 160 that depicts the proper positioning of the defibrillation electrodes 142, 144 on the patient. As will be appreciated from the description below, this layer of user interface component intuitively directs the user to what may become the next appropriate action in the operation of the device and treatment of the patient, namely, depressing the shock key 170 to initiate delivery of a defibrillation pulse to the patient if the electrodes are properly attached and the device detects the presence of a shockable heart rhythm.

Returning to the electrode status display 160, the diagram includes electrode indicators 162, 164 that indicate whether the defibrillation electrodes have been placed on the patient. The electrode indicators 162, 164 can include visual display elements, such as light-emitting diodes, that produce first and second visual signals. For example, the electrode indicators 162 and 164 will display a red light if one of the defibrillation electrodes 142 and 144 has not yet been or is not attached to the patient. Conversely, once the corresponding defibrillation electrode is properly placed on the patient (i.e., the liner has been removed, the electrode attached to the bare-chested patient, and impedance has been detected), the electrode indicators 162, 164 then display a green light.

Figure 9:
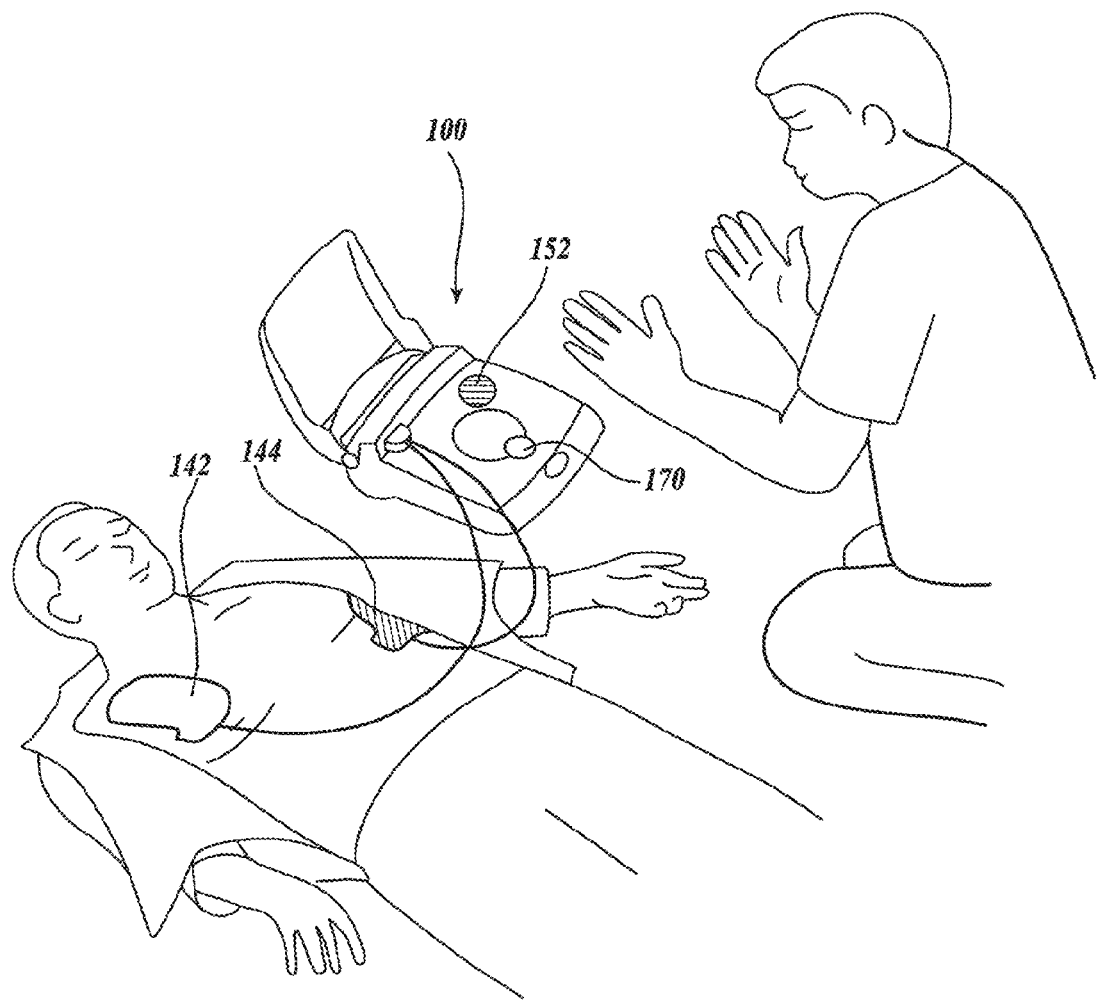
FIG. 9 depicts the defibrillator shown in FIG. 1 while in use by an operator.

Once the electrodes are properly placed on the patient, the AED 100 begins collecting electrocardiogram ("ECG") signals from the patient and analyzing them for a shockable rhythm. FIG. 9 depicts the operator awaiting further device operation and/or treatment instructions from the AED 100. During this time, the AED 100 may issue additional instructions, such as instructions to check the firm adhesion of defibrillation electrodes 142, 144 to the patient, CPR instructions, emergency notification instructions, etc.

If a shockable rhythm is detected, the operator's attention is immediately drawn to the shock key 170 (which is only made available to the operator after the electrode package 120 has been opened and removed from the housing 102) via further visual and/or audible indications. For example, the shock key 170 may be sized, colored and labeled such that it draws the attention of the operator and indicates its function to the operator. For example, the shock key 170 shown in FIG. 6 is prominently sized, centrally placed, contrastingly colored (e.g., red), and includes a diagram depicting an electric shock delivered to a heart. When a shockable rhythm is detected, the shock key 170 may also flash or issue some other suitable visual signal so as to indicate to the operator that he or she can depress the shock key 170 to initiate delivery of a defibrillation pulse to the patient. Additionally, the AED 100 may issue audible instructions to the operator via the audio speaker 152 to depress the shock key 170. Accordingly, it can be appreciated from the above description, that the operator is automatically and intuitively guided by the layered user interface of the present invention from the on/off actuator 108 to the shock key 170, to ultimately initiate delivery of a defibrillation pulse to the patient.

Figure 10:
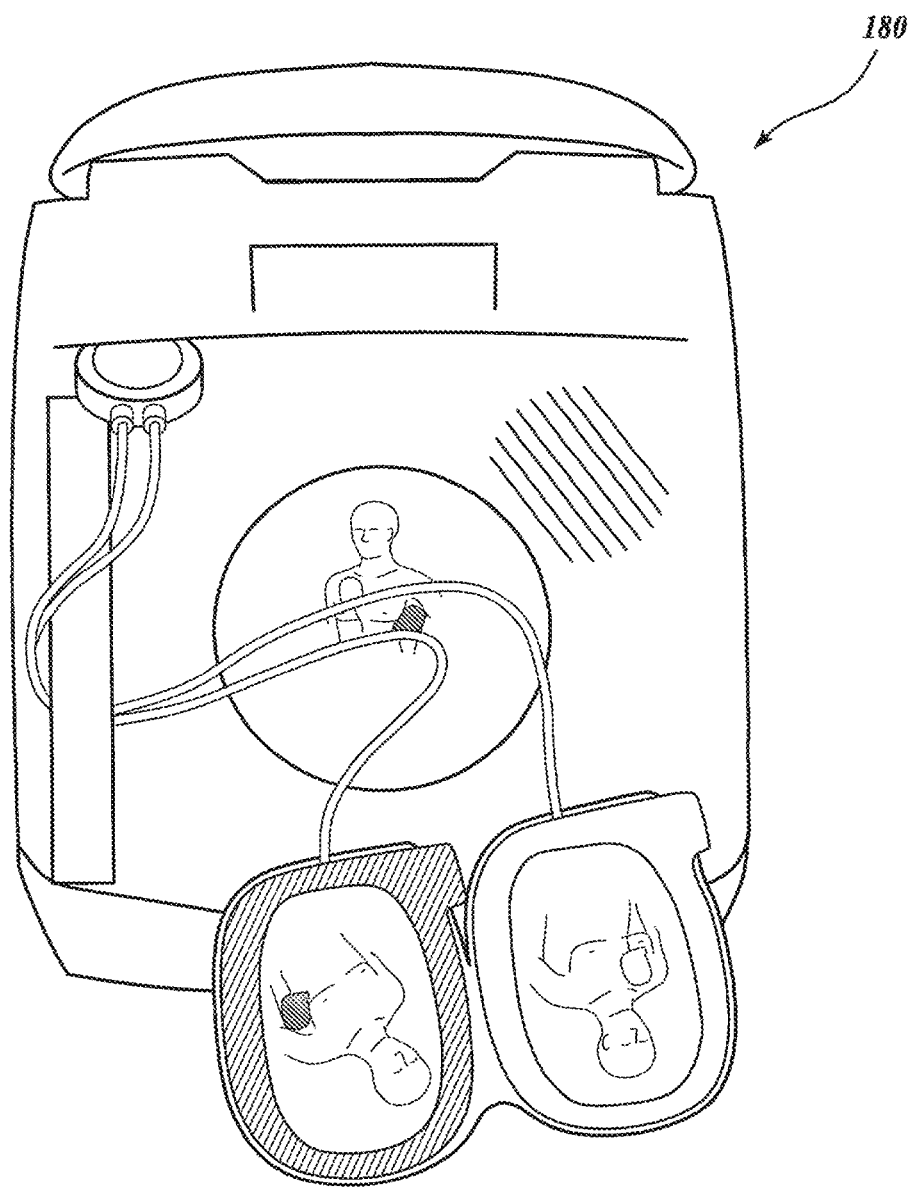
FIG. 10 depicts a fully automatic defibrillator.

It will be appreciated, however, that in another embodiment of the present invention, the AED 100 can be a fully automatic defibrillator (rather than a semi-automatic defibrillator), meaning that the device automatically initiates delivery of a defibrillation pulse to a patient upon detecting a shockable heart rhythm. Accordingly, operator initiation is not required and the shock key 170 is eliminated. A fully automatic AED 180 is shown in FIG. 10, in which no shock key is provided, and in which the AED itself initiates delivery of the defibrillation pulse. The visual and/or audible instructions provided to guide the operator through the delivery of the defibrillation pulse, as well as the shock key 170 if the AED is semi-automatic, may be referred to in the context of the present invention as a "defibrillation pulse delivery layer" of the layered user interface.

Figure 11:
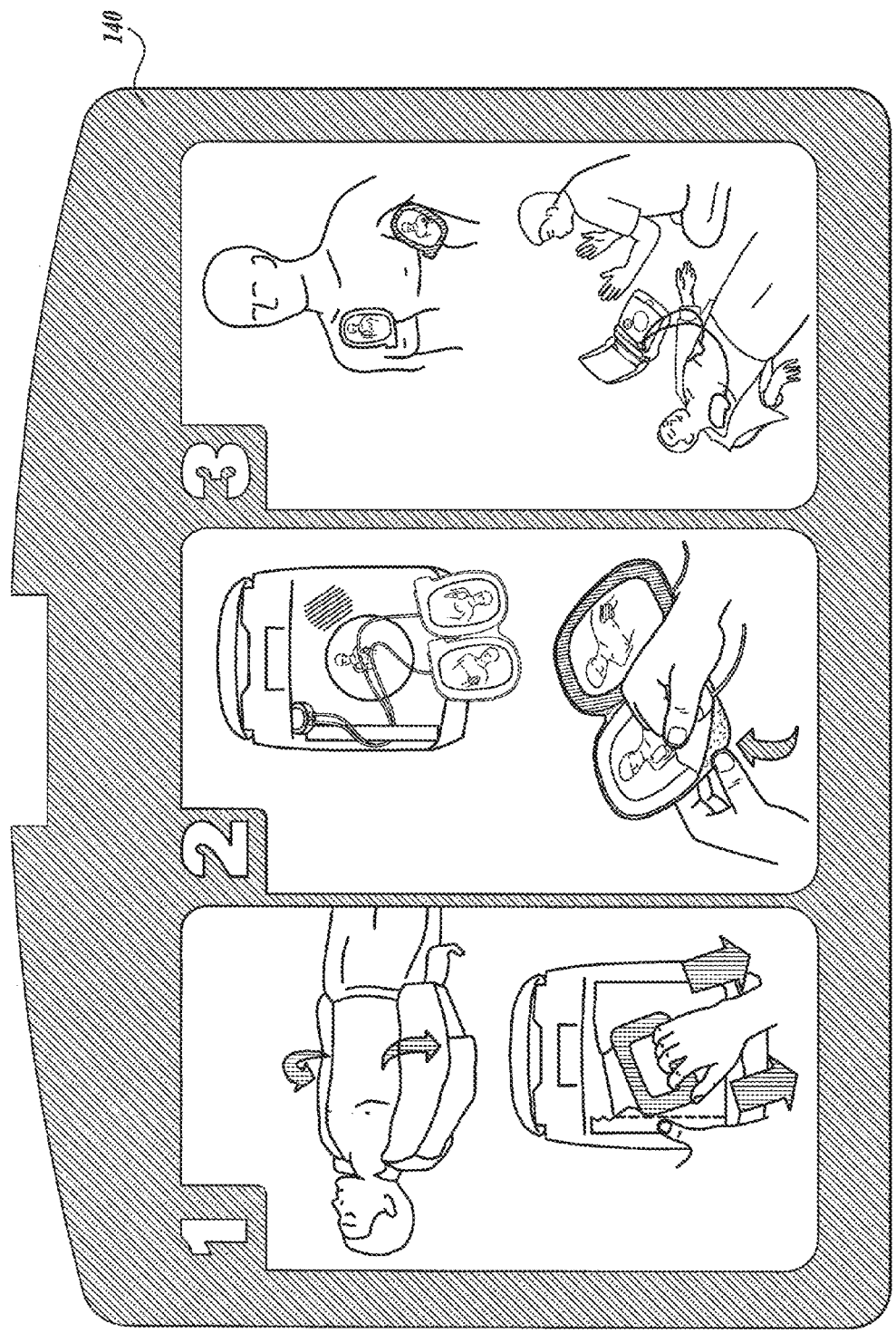
FIG. 11 depicts a reference card mounted on a surface portion of the defibrillator lid made visible to the operator when the lid is opened.

Returning to FIG. 3, given the difficulty a lay person may have opening the electrode package 120, applying the defibrillation electrodes to the patient and operating the AED, the AED 100 may also include another layer of user interface component that is made available to the operator simultaneously with the electrode package 120 when the lid 104 is opened. More specifically, a reference card 140 may be mounted to a bottom surface 138 of the lid 104 that graphically depicts a sequence of the basic instructions to be followed by the operator during use of the AED. FIG. 11 shows a close-up view of the reference card 140. The illustrated embodiment of the reference card 140 depicts the following basic instructions: (1) remove the patient's clothing and pull the handle on the electrode package; (2) remove the electrodes from the package and peel them off the liner; and (3) apply the electrodes to the patient's chest, stand clear and follow the prompts (visual and/or aural) issued by the AED. Accordingly, the operator is given an immediate and always visible idea of what steps must be taken to operate the device and treat the patient. Those skilled in the art will appreciate, however, that the reference card 140 may include any instructions, diagrams, text, etc. deemed desirable by the manufacturer.

In one embodiment of the present invention, the operator is further guided through the layered user interface in the operation of the device and treatment of the patient by a series of audible instructions or voice prompts provided by the AED 100 to the operator via an audio speaker 152 (see FIG. 6), along with electrically driven visual signals, such as the electrode indicators 162, 164 and flashing shock key 170. One skilled in the art will understand that any of a wide variety of combinations of hardware circuitry and software programming can be used to detect or otherwise time the sequence of operator actions and then provide the corresponding signals to the audio speaker 152 and driven visual elements. Particular details of such circuitry and software need not be disclosed for one skilled in the art to understand the teachings of the present invention. However, one example of such circuitry and software as implemented in an AED is described in commonly assigned U.S. Pat. No. 6,334,070, entitled "Visual and Aural User Interface for an Automated External Defibrillator," issued Dec. 25, 2001, and specifically incorporated herein by reference.

Referring to FIG. 12, a flow diagram is presented to depict the sequence of audible and electrically driven visual instructions issued by the AED 100 for the scenario in which a defibrillation shock is actually delivered. A prompting routine 200 is executed by the AED 100, and includes issuing audible instructions via the audio speaker 152 and electrically driven visual instructions via the electrode indicators 162, 164 and flashing shock key 170.

The routine 200 begins in a decision block 210 testing whether the AED 100 has been activated. Once the condition of block 210 is met, the routine 200 continues to block 220, in which the AED 100 issues audible instructions to the operator concerning calling for help, removing clothing to expose the patient's chest, and opening the electrode package 120. The routine 200 continues with a decision block 230 testing whether the electrode package 120 has been opened. If not, the routine 200 returns to block 220.

Once the condition of decision block 230 is met, the routine 200 then continues to block 240, in which the AED 100 issues audible instructions concerning removal of the defibrillation electrodes 142, 144 from the electrode package 120 and removal of the electrodes from the liner 146. The routine 200 then continues to a decision block 250 testing whether the defibrillation electrodes 142, 144 have been removed from the liner 146. If not, the routine 200 returns to block 240 and the appropriate audible instructions are repeated.

Once the condition of decision block 250 is met, the routine 200 then continues with a third instructional step 260, in which the AED 100 issues audible instructions concerning placement of the defibrillation electrodes 142, 144 on the patient's chest and lights up the LEDs 162, 164 of the electrode status display 160 accordingly. The routine 200 continues to a decision block 270 and tests whether the defibrillation electrodes 142, 144 have been properly placed on the patient. If not, the routine 200 returns to block 260 to repeat the appropriate visual and aural instructions to the operator.

Once the condition of decision block 270 is met, the routine 200 continues to block 280, in which the AED 100 issues visual information confirming the proper placement of the defibrillation electrodes 142, 144 (i.e., lights the LEDs of the electrode status display 160 green) and audible information concerning evaluation of the patient's heart rhythm and preparations for delivering a defibrillation pulse. The AED 100 then issues visual instructions (e.g., flashing shock key 170) and audible instructions to the operator to press the shock key 170 and initiate delivery of the defibrillation pulse to the patient.

Those skilled in the art will appreciate that a number of well-known operations are not presented in the flow diagram of FIG. 12, such as instructions relating to patient movement (if detected), decisions by the AED diagnostic circuitry not to shock, instructions relating to CPR, and the like. Such AED operations are described in U.S. Pat. No. 6,334,070, already incorporated herein by reference. Those skilled in the art will further appreciate that various operations can be omitted from the flow diagram of FIG. 12 and performed and/or input by an operator or other device, or substituted with a time-out function without departing from the spirit and scope of the present invention.

While certain embodiments of the invention have been illustrated and described, those skilled in the art will appreciate that various changes can be made without departing from the spirit and scope of the invention. Additional layers of user interface components may be added as appropriate to assist in the operation of the device, treatment of the patient or perhaps the maintenance of the device. For example, as illustrated in FIGS. 1 and 3, the AED 100 may include a readiness display 110 that includes various symbols indicating the status of the AED, such as indicating its readiness for use, the need to replace a battery unit, the need for inspection or repair, or other indication as would be understood by those skilled in the art. The AED 100 may also include a window 112 in the lid 104 through which an electrode expiration date 114 stamped on the upper surface of the electrode package 120 (see FIG. 3) can be seen by the operator when the lid is closed. Together these components may be referred to in the context of the present invention as a "status layer" of the user interface.

We claim:

1. A layered user interface for an external defibrillator comprising:
   an activator that guides an operator to activate the defibrillator, the activator including a lid;
   an electrode application layer made available to the operator subsequent to the activator that guides the operator to apply electrodes to a patient; and
   a defibrillation pulse delivery layer made available to the operator subsequent to the electrode application layer that guides the operator through delivery of a defibrillation pulse to the patient.

2. The layered user interface of claim 1, wherein the activator further includes an on/off actuator used by the operator to activate the defibrillator.

3. The layered user interface of claim 2, wherein the on/off actuator is a button contrastingly configured and colored to draw the attention of the operator.

4. The layered user interface of claim 1, wherein the electrode application layer comprises an electrode package containing the electrodes, and instructions for opening the package and for applying the electrodes to the patient.

5. The layered user interface of claim 4, wherein the instructions include audible instructions.

6. The layered user interface of claim 4, wherein the instructions include visual instructions.

7. The layered user interface of claim 4, wherein the instructions include written instructions.

8. The layered user interface of claim 4, wherein the instructions include diagrammatic instructions.

9. The layered user interface of claim 1, wherein the defibrillation pulse delivery layer comprises a shock key actuatable by the operator to initiate delivery of the defibrillation pulse, and instructions for actuating the shock key.

10. The layered user interface of claim 9, wherein the instructions include visual instructions.

11. The layered user interface of claim 9, wherein the instructions include audible instructions.

12. The layered user interface of claim 1 further comprising a status layer that indicates to the operator the status of the defibrillator.

13. The layered user interface of claim 12, wherein the status layer comprises a readiness display which indicates the status of components of the defibrillator.

14. A layered user interface, for an external defibrillator comprising:
- an activation layer that guides an operator to activate the defibrillator;
- an electrode application layer made available to the operator subsequent to the activation layer that guides the operator to apply electrodes to a patient;
- a defibrillation pulse delivery layer made available to the operator subsequent to the electrode application layer that guides the operator through delivery of a defibrillation pulse to the patient; and
- a status layer that indicates to the operator the status of the defibrillator, wherein the status layer comprises an electrode expiration date display that indicates the status of the defibrillator's electrodes.

15. The layered user interface of claim 1, wherein the defibrillation pulse delivery layer comprises instructions for guiding the operator through delivery of the defibrillation pulse, wherein the defibrillator automatically initiates delivery of the defibrillation pulse.

\* \* \* \* \*